(12) United States Patent
Blondeau et al.

(10) Patent No.: US 10,576,179 B2
(45) Date of Patent: Mar. 3, 2020

(54) RELATING TO ORGANIC COMPOUNDS

(71) Applicant: Givaudan, S.A., Vernier (CH)

(72) Inventors: Philippe Blondeau, Paris (FR); Alice Bresson Boil, Herblay (FR); Andras Borosy, Duebendorf (CH); Celine Ropartz-Lebel, Taverny (FR); Michele Brubaker, Allendale, NJ (US)

(73) Assignee: Givaudan, S.A., Vernier (CH)

( * ) Notice: Subject to any disclaimer, the term of this patent is extended or adjusted under 35 U.S.C. 154(b) by 32 days.

(21) Appl. No.: 15/809,272

(22) Filed: Nov. 10, 2017

(65) Prior Publication Data
US 2018/0078666 A1 Mar. 22, 2018

Related U.S. Application Data

(63) Continuation-in-part of application No. PCT/EP2016/060585, filed on May 11, 2016.

(60) Provisional application No. 62/160,908, filed on May 13, 2015.

(51) Int. Cl.
*A61L 9/03* (2006.01)
*C11B 9/00* (2006.01)
*A61L 9/01* (2006.01)

(52) U.S. Cl.
CPC ............... *A61L 9/037* (2013.01); *A61L 9/01* (2013.01); *C11B 9/00* (2013.01)

(58) Field of Classification Search
CPC ............... A61L 9/037; A61L 9/01; C11B 9/00
See application file for complete search history.

(56) References Cited

U.S. PATENT DOCUMENTS

| | | | |
|---|---|---|---|
| 7,740,395 B2* | 6/2010 | Samuel | A61L 9/03 362/101 |
| 8,603,963 B1 | 12/2013 | Steward et al. | |
| 9,115,329 B2 | 8/2015 | Chapuis | |
| 9,243,210 B2 | 1/2016 | Chapuis | |
| 9,868,923 B2* | 1/2018 | Blondeau | C11B 9/0003 |
| 2003/0175395 A1 | 9/2003 | Starkenmann | |
| 2010/0204344 A1* | 8/2010 | Kraft | C11B 9/0084 514/772 |
| 2010/0291016 A1 | 11/2010 | Moretti | |
| 2011/0091404 A1* | 4/2011 | Wohrle | A61K 8/37 424/70.1 |
| 2011/0092604 A1* | 4/2011 | Wohrle | C11B 9/0034 514/772 |
| 2011/0104089 A1* | 5/2011 | Wohrle | A61K 8/375 424/60 |
| 2012/0077722 A1* | 3/2012 | Dilk | A61L 2/16 510/103 |
| 2013/0036911 A1 | 2/2013 | Mak | |
| 2013/0052151 A1* | 2/2013 | Narula | C11D 3/50 424/76.2 |
| 2013/0065807 A1* | 3/2013 | Eh | A61K 8/33 510/104 |
| 2013/0202543 A1* | 8/2013 | Kuper | A61K 8/345 424/70.1 |
| 2013/0261036 A1* | 10/2013 | Holscher | A61K 8/37 510/106 |
| 2013/0336910 A1* | 12/2013 | Chatelain | G01N 33/566 424/65 |
| 2013/0336911 A1* | 12/2013 | Behan | C11B 9/0023 424/65 |
| 2014/0135402 A1 | 5/2014 | Fankhauser | |
| 2014/0221262 A1 | 8/2014 | Chapuis | |
| 2014/0323768 A1* | 10/2014 | Narula | C11D 3/50 568/375 |

(Continued)

FOREIGN PATENT DOCUMENTS

WO WO 2013/020774 A1 2/2013
WO WO 2014/023967 A1 2/2014

(Continued)

OTHER PUBLICATIONS

Computer Aided Fragrance Design (1-112pages) Koscak Naja Univ. Prof. Mag Pharm. Gerhard Buchbauer (Year: 2011).*

(Continued)

*Primary Examiner* — Pamela H Weiss
(74) *Attorney, Agent, or Firm* — Curatolo Sidoti Co., LPA; Salvatore A. Sidoti

(57) ABSTRACT

A liquid electrical air care device for dispensing a liquid composition from a reservoir containing the liquid composition, wherein the liquid composition includes 0.1% to 10% by weight of the total liquid composition of a fragrance ingredient having a standard equilibrium headspace concentration ($HS_i$) of greater than 12 to 50 micrograms/litre and a Flexibility Index ($FI_i$) of 45 or more, and/or 0.1% to 7% by weight of the total liquid composition of a fragrance ingredient having a standard equilibrium headspace concentration ($HS_i$) between 5 and 12 micrograms/litre and a Flexibility Index ($FI_i$) of between 20 and 44, and/or 0 to 1% by weight of the total liquid composition of a fragrance ingredient having a standard equilibrium headspace concentration ($HS_i$) of less than 5 micrograms/litre and a Flexibility Index of between 7 and 19 ($FI_i$).

8 Claims, No Drawings

(56) References Cited

U.S. PATENT DOCUMENTS

| | | |
|---|---|---|
| 2015/0152352 A1 | 8/2015 | Huboux et al. |
| 2015/0157756 A1 | 8/2015 | Duffield et al. |
| 2015/0322375 A1 | 11/2015 | Chapuis |

FOREIGN PATENT DOCUMENTS

| | | | |
|---|---|---|---|
| WO | WO 2014/124834 A1 | 8/2014 | |
| WO | WO-2014198709 A1 * | 12/2014 | ............. C07C 45/82 |

OTHER PUBLICATIONS

PCT/EP2016/060585—International Search Report, dated Oct. 19, 2016.
PCT/EP2016/060585—International Written Opinion, dated Oct. 19, 2016.
Great Britain Search Report GB1510416.9—Search Report, dated Dec. 16, 2015.
Labute, Paul, "LowModeMD-Implicit Low-Mode Velocity Filtering Applied To Conformational Search Of Macrocycles And Protein Loops", J. Chem Inf. Model., Apr. 29, 2010, pp. 792-800, vol. 50.

* cited by examiner

RELATING TO ORGANIC COMPOUNDS

CROSS REFERENCE TO RELATED APPLICATIONS

This application is a bypass Continuation-In-Part application of International Application No. PCT/EP2016/060585, filed 11 May 2016, which claims priority from U.S. Provisional Patent Application No. 62/160,908, filed 13 May 2015, which applications are incorporated herein by reference.

The present invention generally relates to fragrance-containing liquid formulations, adapted to be dispensed from air freshener devices, particularly electrical air freshener devices.

Devices designed to dispense fragrance materials into ambient air thereby to impart a desirable and pleasant fragrance are well known in the art. Such devices, commonly known as air fresheners or room deodorizers, are commercially available in a variety of forms. A particular type of device is the so-called "plug in" or "liquid electrical" device. They typically comprise a fragrance-containing liquid formulation that is held in a container or reservoir. A wicking means may extend out of the container into proximal relationship with a heating element, which is typically powered by mains electricity or is battery powered. The liquid formulation is drawn up the wicking means to a position proximal to a heating element, and heat from the heating element causes accelerated evaporation of the fragrance thereby to disperse the fragrance into the ambient atmosphere.

Whatever the particular design of these devices, or the particular mechanism of fragrance emanation, it is imperative that they perform in a manner that allows fragrance material to be dispensed at a steady and controlled rate into an environment, and that the fragrance maintains its odour integrity over the life span of the device. Furthermore, all fragrance material should be consumed, or substantially consumed, at the end of the useful life of a device.

However, these functions are difficult to achieve, and most commercially available devices suffer from similar limitations, notably, that the odour becomes distorted over the life span of the device due to the fact that the more volatile ingredients of a fragrance formulation emanate faster than the less volatile ingredients, leaving behind residues of the less volatile ingredients in the reservoir or in the wicking means. These compositional changes of the fragrance formulation, over time, create a loss of freshness and change in the character of the fragrance emitted into the ambient atmosphere. These problems have occupied much of the attention of those who seek to devise better air freshener devices.

Various efforts have been made to overcome these problems. From a fragrance design perspective, it has been proposed to use only fragrance ingredients having similar volatility to ensure that substantially all ingredients evaporate at the same rate. Solvents or carriers have also been proposed to aid in the uniform evaporation of fragrance ingredients.

However, certain fragrance ingredients, especially those which tend to be at the upper end of the molecular weight range, or the lower end of vapour pressure range of fragrance ingredients, are generally regarded in the art as being difficult to use in air freshener applications because they migrate very slowly or not at all along the wick, and fragrance formulations containing them at any appreciable levels display unacceptably low rates of evaporation. This is particularly the case of musk ingredients and ingredients displaying heavy oriental, woody and amber notes.

As such, despite the myriad types and designs of air-freshener devices, such as plug-in devices, on the market, using such musk ingredients remains a difficult challenge.

On the other hand, musky ingredients form a very important class of perfumery ingredients that provide warmth and depth to perfume scents. Limiting their use, due to above mentioned technical issues, leads to undesired limitation of the palette of odours accessible to the perfumers. In particular, certain hedonic directions, such as those reminiscent of fine fragrances, or of caring and elegant ambiances are not easily achievable without the use of musk ingredients. This is an issue today in the fast moving market dynamics of the air-freshener business. Consumers of air freshener devices are no longer satisfied with their devices merely providing an odour eliminating or deodorizing effect and are increasingly looking for products providing a home signature and an expression of self.

There is, therefore, a need to provide perfume formulators with a wider palette of ingredients, which they can use to create market differentiating olfactive impressions. Fragrance ingredients that can provide typical base note olfactive impressions of softness, warmth, solidity and depth, and those particularly that are in the woody, chypre or musk olfactive direction, are increasingly sought after fragrance ingredients for use in air-freshener devices in order to achieve differentiation in a competitive landscape.

Fragrance formulations intended for air freshener applications containing these types of ingredients and which are nevertheless both long-lasting, impactful and which deliver a coherent fragrance impression throughout the life of a device remain technically challenging and elusive.

In addressing the shortcomings in the art, the applicant surprisingly discovered that molecular weight and vapour pressure of ingredients do not adequately explain the performance of high molecular weight and/or low vapour pressure fragrance ingredients in air freshener devices. More particularly, applicant found that the conformational mobility (the flexibility) of a fragrance ingredient was a reliable indicator of performance. With this insight, applicant was able to create long-lasting and impactful fragrance formulations that could deliver olfactive impressions of softness, warmth, solidity and depth, which drive customer liking. Furthermore, delivery of these olfactive impressions to ambient air can be achieved over a long period of time and without noticeable change in the rate of delivery or odour character during the useful life of a device. Furthermore, applicant found that it was possible to create fragrance formulations having these desirable properties and performance characteristics, despite the restrictions imposed by regulation, most notably those mandated by the CARB regulation in the United States.

Accordingly, the invention provides in a first aspect a liquid composition suitable for use in an electrical plug-in air freshener device comprising at least one fragrance ingredient selected from the group consisting of:

0.1% to 10% by weight of the total liquid composition of a fragrance ingredient, which is an Ingredient Group 1 ingredient; or 0.1% to 7% by weight of the total liquid composition of a fragrance ingredient, which is an Ingredient Group 2 ingredient; or 0 to 1% by weight of the total liquid composition of a fragrance ingredient, which is an Ingredient Group 3 ingredient;

wherein an ingredient Group 1, is a fragrance ingredient, having a standard equilibrium headspace concentration ($HS_i$) of greater than 12 to 50 micrograms/litre, and a known Flexibility Index ($FI_i$) of 45 or more;

an ingredient Group 2, is a fragrance ingredient having a standard equilibrium headspace concentration ($HS_i$) between 5 and 12 micrograms/litre, and a known Flexibility Index of 20 or greater, and more particularly between 20 and 44;

an ingredient Group 3, is a fragrance ingredient having a standard equilibrium headspace concentration ($HS_i$) of less than 5 micrograms/litre, and a known Flexibility Index of 7 or greater, and more particularly between 7 and 19;

The standard equilibrium headspace concentration ($HS_i$), expressed in microgram/litre, refers to the concentration of the ingredient in equilibrium with the condensed form, that is in solid or liquid form, of this ingredient at a temperature of 25° C. and under a pressure of 1 atmosphere. It can be measured by using any of the known quantitative headspace analysis techniques in the art. A suitable method is described in Mueller and Lamparsky in Perfumes: Art, Science and Technology, Chapter 6 "The Measurement of Odors" at pages 176-179 (Elsevier 1991).

Typically, an equilibrium headspace concentration may be measured as follows: 500 mg of the test compound is added to a headspace container which is then sealed. The container is then incubated at constant 25° C. until the compound reaches equilibrium between the gas and the liquid phase. A defined volume of this saturated headspace (usually 0.5-1 lt) is trapped on a micro filter using Porapak Q as sorbent. After filter extraction with an appropriate solvent (usually 30-100 microliters methyl tertiary butyl ether), an aliquot of the extract is analyzed by GC. Quantification is performed by the external standard calibration method. The concentration in the original headspace can be calculated (in terms of microgram/litre) from the headspace volume sucked through the micro filter and the aliquot of the filter extract injected into the gas chromatograph. The final headspace concentration value of a given test compound is obtained as the mean value of three independent measurements each. Further information of the technique hereinabove described may be found in the article of Etzweiler, F.; Senn E. and Neuner-Jehle N., *Ber. Bunsen-Ges. Phys. Chem.* 1984, 88, 578-583.

Knowing the molecular weight of a compound, the standard equilibrium headspace concentration is related to the partial vapour pressure of the compound by the State of Gases equation, which in a first and suitable approximation is given by the law of ideal gases.

The Flexibility Index can be calculated as follows: First, the structure of each ingredient is minimized by applying the default setting of the Energy minimisation menu in MOE (Molecular Operating Environment, Chemical Computing Inc.) by using the MMFF94 force field. As molecular surface depends heavily on 3D structures, the conformations of each molecule are generated by the default setting of Low-ModeMD search in MOE (see P. Labute, P. "Low-ModeMD—Implicit Low Mode Velocity Filtering Applied to Conformational Search of Macrocycles and Protein Loops". *J. Chem. Inf. Model.* 50 (2010) 792-800). Finally the water accessible surface area values (ASA) of each conformation is computed in MOE by using a radius of 1.4 Å for the water molecule. The range of ASA (difference of maximum and minimum values) of a molecule is a reliable measure of flexibility.

The conformational mobility (as represented by the Flexibility Index) of fragrance ingredients is a useful parameter that has not be utilised heretofore in the design of fragrance formulations useful in air freshener devices. Surprisingly, however, the applicant found that perfume ingredients having relatively low vapour pressure, corresponding for example to a standard headspace equilibrium concentrations less than 50 microgram/l, which might otherwise be disregarded by perfumers for use in air fresheners, can be used sparingly, and yet effectively, by having due regard to the conformational mobility of the ingredients. For example, ingredients having a vapour pressure of less than 5 micrograms/litre, can only be employed in very small amounts, if at all, if they have a Flexibility Index lower than about 45, but ingredients with similarly low vapour pressure can be used an quite high amounts (up to about 10%) if they are conformationally more mobile (for example a Flexibility Index around 70 to 80, or even higher).

A particular class of fragrance ingredients that can be exploited more fully in air freshener perfumery as a result of this finding is the class of musk ingredients. Musks are highly valued molecules in perfumery and are used as base notes in all manner of applications. And yet, they are under-utilised in air freshener applications. By means of the present invention, applicant has been able to produce fragrance formulations containing musk ingredients and as a result has been able to produce highly differentiated olfactive impressions, which drive liking in consumer tests.

Accordingly, in a particular embodiment of the present invention the Ingredient Group 1, 2 and 3 ingredients referred to hereinabove are selected from musk ingredients.

Musk ingredients according to the present invention include those selected from the group consisting of Cashmeran (FI 3.2), Galaxolide S (FI 3.9), Moxalone (FI 7.8), Cosmone (FI 23.3), Thibetolide (FI 29.5), Velvione (FI 30.3), Rosamusk (FI 30.4), Muscenone (FI 34.7), Nirvanolide (FI 35.1), Habanolide (FI 35.6); Civettone (FI 37.2); Musk C14 (FI 39.3); Ethylene Brassylate (FI 44.7); Ambrettolide (FI 44.7); Pentambrette (FI 65.1), 2-(1-(3,3-dimethylcyclohexyl)ethoxy)-2-methylpropyl acrylate (FI 69.2), Serenolide (FI 74.9), Applelide (FI 76.2) and Sylkolide (FI 81.6); Romandolide (FI 82.9), Citronellyl ethoxalate (FI 118.5), Cyclomusk (FI 122.5) and Silvanone (a mixture of Musk CPD (FI 25.4) and Hexadecanolide (FI 36.6) in iso-propyl myristate), (R,E)-2-methyl-2-((3-methylhex-3-en-2-yl)oxy)propyl cyclopropanecarboxylate (FI 82.4), (R,E)-2-((3-ethyl-5-methylhex-3-en-2-yl)oxy)-2-methyl-propyl cyclopropanecarboxylate (FI 86.3), (R,E)-2-((3-ethyl-5-methylhex-3-en-2-yl)oxy)-2-methylpropyl propionate (FI 84.3), (R,E)-2-((3-ethyl-5-methylhex-3-en-2-yl)oxy)-2-methylpropyl cyclobutanecarboxylate (FI 109.4), (R,E)-2-((3,6-dimethylhept-3-en-2-yl)oxy)-2-methylpropyl cyclopropanecarboxylate (FI 104, 1), (E)-2-((3,5-dimethyl-hept-3-en-2-yl)oxy)-2-methylpropyl cyclopropanecarboxylate (FI 99.1), 2-((4-(cyclohex-3-en-1-yl)-3-methylbut-3-en-2-yl)oxy)-2-methylpropyl isobutyrate (FI 101.9).

In particular embodiments, suitable musk notes include those selected from the group Cashmeran (1,1,2,3,3-pentamethyl-2,3,6,7-tetrahydro-1H-inden-4(5H)-one), Galaxolide (4,6,6,7,8,8-hexamethyl-1,3,4,6,7,8-hexahydrocyclopenta[g]isochromene), Galaxolide S ((4S)-4,6,6,7,8,8-hexamethyl-1,3,4,6,7,8-hexahydrocyclopenta[g]-2-benzopyran), Moxalone (1a,3,3,4,6,6-hexamethyl-1a,2,3,4,5,6,7,7a-octahydronaphtho[2,3-b]oxirene), Cosmone ((Z)-3-methylcyclotetradec-5-enone), Thibetolide (oxacyclohexadecan-2-one), Velvione ((Z)-cyclohexadec-5-enone), Muscenone ((Z)-3-methylcyclopentadec-5-enone), Nirvanolide ((E)-13-methyloxacyclopentadec-10-en-2-one), Habanolide ((E)-oxacyclohexadec-12-en-2-one), Civettone ((Z)-cycloheptadec-9-enone), C14 musk (1,4-dioxacyclohexadecane-5,16-dione), Ethylene brassylate (1,4-dioxacycloheptadecane-5,17-dione), Ambrettolide ((Z)-oxacycloheptadec-10-en-2-one), Serenolide (2-(1-(3,3-dimethylcyclohexyl)ethoxy)-2-methylpropyl cyclopropanecarboxylate), Sylkolide ((E)-2-((3,5-dimethylhex-3-en-2-yl)oxy)-2-methylpropyl cyclopropanecarboxylate), Silvanone (blend of cyclopentadecanone and 1-oxacycloheptadecan-2-one), Musk CPD (cyclopentadecanone), Hexadecanolide (1-oxacycloheptadecan-2-one) and mixtures thereof.

In an embodiment of the present invention the liquid composition contains 0.1 to 10% by weight of one or more of Sylkolide, Helvetolide, Serenolide or Moxalone.

In an embodiment of the present invention, the liquid composition contains 0.1 to 7%, and more particularly 0.1 to 3% of Muscenone.

In an embodiment of the present invention, the liquid composition contains 0.1 to 7%, and more particularly 3 to 5% of one or more of Silvanone supra (a 60% mixture of hexadecanolide and cyclopentadecanolide in iso-propyl myristate), Nirvanolide and Cosmone.

In an embodiment of the present invention, the liquid composition contains 0.1 to 7%, and more particularly 5 to 7% of one or more of Fixolide, Serenolide and Thibetolide.

In an embodiment of the present invention, the liquid composition contains up to 1% of Habanolide.

In an embodiment of the present invention, the liquid composition contains one or more musk compounds as herein above described, provided it is not Galaxolide S, Musk C14, Ethylene brassylate, Ambrettolide and Velvione.

The total amount of fragrance ingredients referred to herein above may be present in the liquid composition in amounts of up to 100%, more particularly up to 90% and still more particularly up to 80%.

The liquid composition according to the present invention, in addition to the fragrance ingredients referred to hereinabove, may contain one or more other fragrance ingredients having a standard equilibrium headspace concentration at 25° C. that is less than 104 micrograms per litre (mug/l). Suitable fragrance ingredients are set forth in S. Arctander "Perfume and Flavor Chemicals: Volume 1, Allured Publishing Corporation 1969, or any later editions thereof, as well as the IFRA (International Fragrance Research Association) database, and RIFM (Research Institute of Fragrance Materials) database, each of which and hereby incorporated by reference in their entirety.

The liquid composition according to the present invention may contain one or more solvents or carriers to aid the evaporation of the fragrance ingredients mentioned hereinabove and in particular solvents having vapour pressure less than 0.6 mm Hg and still more particularly less than 0.1 mm Hg, and more particularly those which are included as approved for use by the California Air Resources Board (CARB) as so-called LVPVOC "low vapour pressure volatile organic compound". Examples of such solvents are set forth in U.S. Pat. No. 8,603,963, which is hereby incorporated by reference.

Examples of suitable solvents include dipropylene glygol, propylene glycol, glycol esters and glycol ethers available commercially from Dow Chemicals under the name Dowanol®, such as Dowanol® DPMA (dipropylene glycol methyl ether acetate), Dowanol® DPM (dipropylene glycol methyl ether), Dowanol® TPM (tripropylene glycol methyl ether), Dowanol® DPNB (propylene glycol n-butyl ether, Dowanol® DPNP (propylene glycol n-propyl ether), and other suitable Dow Chemical Dow P-series glycol ethers, dibasic ester DBE (blend composed of diisobutyl glutarate, diisobutyl succinate, and diisobutyl adipate, commercially available from Solvay, or blend composed of diisobutyl glutarate, and diisobutyl adipate, commercially available from Invista), methyl methoxy butanol(+/−)-2,2-dimethyl-4-hydroxymethyl-1,3-dioxolane, commercially available from Solvay under the name Augeo Clean Multi, dimethyl isosorbide, and mixture thereof.

The solvent may be present in amounts of 10% or more based on the total weight of the liquid formulations, more particular 20% or more, still more particularly 30% or more. The upper range of low vapour pressure solvent may be up to 60%, more particularly up to 70% and still more particularly up to 80% based on the total weight of the liquid formulation of the present invention.

In addition to, or in place of said solvents, a liquid formulation of the present invention may contain one or more carrier perfume ingredients, which have similar evaporation properties as the above mentioned solvents. Suitable carrier perfume ingredients include Dipentene (138-86-3), Terpinolene (586-62-9), Ethyl acetoacetate (141-97-9), Hexyl acetate (142-92-7), Florosa HC (63500-71), Ethyl heptanoate (106-30-9), Ethyl capronate (123-66-0), Freskomenthe (14765-30-1), Bornyl acetate liquid (125-12-2), Benzyl acetate (140-11-4), Diethyl malonate (105-53-3), Linalool (78-70-6), Dihydro myrcenol (18479-58-58), Linalyl acetate (115-95-7), Limonene (5989-54-8), Agrumex (88-41-5), Ethyl linalool (10339-55-5), Jasmacyclene (5413-60-5), Para tert-butyl-cyclohexyl acetate (32210-23-4), and Nonanyl acetate (58430-94-7). The numbers in parentheses are CAS numbers.

If any of these carrier perfume ingredients are present in a liquid formulation according to the invention, they may be present in amounts of 10% or more based on the total weight of the liquid formulations, more particular 20% or more, still more particularly 30% or more. The upper range of said ingredients may be up to 60%, more particularly up to 70% and still more particularly up to 80% based on the total weight of the liquid formulation of the present invention.

In an embodiment of the present invention the liquid composition comprises iso-nonylacetate, dihydromyrcenol, linalool, geraniol, d-limonene, benzyl acetate, and mixtures thereof. Preferably, iso-nonylacetate, dihydromyrcenol, linalool, geraniol, d-limonene, benzyl acetate, and mixtures thereof, is present in amounts of 10% or more based on the total weight of the liquid formulations, more particular 20% or more, still more particularly 30% or more.

The liquid formulation according to the present invention may additionally comprise one or more volatile aroma chemicals having a high volatility, e.g. a vapour pressure at 25 degrees centigrade of 0.1 mmHg or higher, more particularly at least about 0.2 mmHg, or at least about 0.5 mmHg, or at least 1 mmHg. Exemplary volatile aroma chemicals include hexyl acetate, 3,3,5-trimethylhexyl acetate, bornyl formate, 3-hexenyl butyrate, phenyl ethyl acetal, butyl hexanoate, isononanol, acetone alcohol, isoprenyl acetate, isobutyl 2-pentanoate, amyl propionate, herbal dioxane, furfuryl formate, methyl acetyl acetone, and butyl acetoacetate.

Other volatile aroma chemicals may be selected from any of the compounds known as LVPVOC potentiator compounds set forth in U.S. Pat. No. 8,603,963, and in particular Table 1 of this patent document, which is hereby incorporated by reference.

The volatile aroma chemicals may be present in amounts of 10% or more based on the total weight of the liquid formulations, more particular 20% or more, still more particularly 30% or more. The upper range of said ingredients may be up to 60%, more particularly up to 70% and still more particularly up to 80% based on the total weight of the liquid formulation of the present invention.

In an embodiment of the present invention the liquid composition comprises one or more fragrance ingredients selected from a group 1 and/or group 2 and/or a group 3 ingredient; at least one other fragrance ingredient having a standard equilibrium headspace concentration at 25° C. that is less than $10^4$ mug/l; a low vapour pressure solvent, and optionally at least one of said volatile aroma chemicals.

In an embodiment of the present invention the liquid composition comprises one or more fragrance ingredients selected from a group 1 and/or group 2 and/or a group 3 ingredient; at least one other fragrance ingredient having a standard equilibrium headspace concentration at 25° C. that is less than $10^4$ mug/l; and at least one perfume ingredient referred to hereinabove as a carrier perfume ingredient.

In addition to the aforementioned materials, liquid formulations of the present invention may contain one or more active agents selected from the group consisting of an agent that provides fabric conditioning or softening, fabric refreshing, air freshening or deodorising, malodour removal. Active agents might also include surfactants emulsifiers, solubilizers, polymers, malodour counteracting agents, buffers, zinc ions, and the like.

In a further aspect, the present invention provides a liquid electrical air care device comprising a reservoir containing a liquid composition as defined above.

Air care devices suitable for use with liquid compositions according to the present invention include electrical air freshening devices, which refers to a device or system that includes an electrical or battery source of energy. The term "electrical air freshening device includes heated liquid wick systems, piezoelectrical spraying systems, electrospray devices and Venturi devices, as well as devices that are powered by solar or other alternative forms of energy.

Any suitable size, shape, form, or configuration of device can be used. Suitable devices can be made from any suitable material, including but not limited to: natural materials, man-made materials, fibrous materials, non-fibrous materials, porous materials, non-porous materials, and combinations thereof.

In certain embodiments, a typical device utilizes a combination of a wick, and an emanating surface to dispense a liquid composition from a liquid composition reservoir.

Devices (such as, "wicking devices") are known for dispensing volatile liquids into the atmosphere, such as fragrance, deodorant, disinfectant, or insecticide active agent. A typical air care device utilizes a combination of a wick and emanating surface to dispense a volatile liquid from a liquid fluid reservoir. Devices should perform in a manner that allows the liquid composition to be dispensed at a steady and controlled rate into an ambient atmosphere while maintaining a coherent olfactive profile over the life span of the device.

In an embodiment of the invention, a device includes an electrical or battery operated source of energy which includes heated liquid wick delivery systems, piezoelectrical spraying systems, electrospray devices or Venturi devices. Commercial examples of electrical liquid air freshner devices include, but are not limited to, Glade® PlugIns® Scented oil, sold by SC Johnson & Sons; Air Wick Scented Oils, and Air Wick X-Press® Scented Oils, sold by Reckitt Benckiser; Febreze Noticeables sold by Proctor & Gamble Co., Electric Home Air Fresheners, sold by the Yankee Candle Co.; and Renuzit Scented Oils, sold by Henkel AG.

Liquid compositions according to the present invention find utility as perfumes that can be dispensed from all manner of fragrance dispensing devices referred to hereinabove. The liquid compositions provide a headspace in an ambient atmosphere which is long-lasting, meeting desired intensity levels but with a soft, deep and warm character with low harsh/chemical associations. Ordinarily, perfumes that are used in air care devices suffer in the market place because the required perfume intensity has to be traded off against the harsh chemical character of the perfume. Conversely, liquid compositions of the present invention manage to provide a strong, long-lasting olfactive profile, which is at the same time soft and lacking in undesirable chemical character.

Liquid compositions according to the present invention evaporate in a controlled fashion. In particular, the evaporation rate, measured as weight of fragrance loss, per unit of time ranges from 0.2-0.6 g/day over a given time period, e.g., 30, 40 or 60 days, is relatively constant over the given time period. Evaporation rates are substantially constant, for example weight of fragrance loss per unit of time differs by less than +-5%, or +-10% or +-20% over the given time period.

Furthermore, evaporation rates are such that the reservoir containing liquid composition according to the invention is empty, or substantially so, before the rate decays to a level below 0.2 g/day.

There now follows a series of examples that further illustrate the invention:

EXAMPLE 1

Evaporation Profiles:

Evaporation tests were carried out using a market product heating unit, consisting of vessel containing 25 ml perfume, the top of this vessel being closed by a cap comprising the electrical heating element and a channel for the wick. The unit further comprises a polyester fibre wick (ex ESSENTRA®), disposed in such a way that one end the wick is dipped into the perfume and the other end is in contact with the air, whereas the end of the wick in contact with the air is also surrounded by or close to the electric heating unit.

Heating temperature at the top of the wick was set at 80 degrees centigrade. All ingredients were tested at equal dosages corresponding to 10% in solvent (Dowanol® TPM, (tripropylene glycol methyl ether) commercially available from Dow Chemicals). Three experiments were carried out per ingredient and the values reported represent average values.

Weight loss was calculated as a function of time (weight loss/day). Once evaporation rate reached 0.02 g/day, evaporation was deemed to have ceased. The percentage of ingredient remaining in its reservoir once the evaporation rate reached 0.02 g/day was recorded. The time (days) to reach this threshold was likewise recorded.

Two linear musk molecules (Sylkolide and Helvetolide) and a bicyclic musk molecule (Moxalone) left no residue at all in their respective reservoirs. The time (days) to reach the threshold was 23, 28 and 26 respectively. The results indicate that these molecules are eminently suitable for use in air freshener devices and can be used freely at levels at which they can significantly impact the hedonics, long-lastingness and impact of the olfactive profile of a fragrance formulation.

Five macrocyclic musks (S Galaxolide, Musk C14, Ethylene Brassylate, Abrettolide and Velvione) left residues (wt %) of 14.5, 9.5, 10.0, 9.5 and 11.0 respectively. The time (days) to reach threshold was 30, 36, 37, 43 and 55 respectively. The results indicate that these molecules should be used sparingly (1% or less) or preferably not at all as their use is inefficient (significant residue in reservoirs) and cause significant clogging of the wicks.

A further group of macrocyclic musk molecules (Muscenone, Silvanone Supra, Nirvanolide and Cosmone) left residues (wt %) of 6.0, 2.0, 3.5 and 4.5 in a time to threshold (days) of 45, 50, 38 and 35 respectively. The results indicated that these molecules behave in a somewhat intermediate fashion and should be used sparingly, e.g. up to about 3 to 5%, as although they do not exhibit clogging of wicks, nevertheless their use can result in delay in evaporation.

A final group of musks (bicyclic, linear and macrocyclic) (Fixolide, Serenolide and Thibetolide) left residues (wt %) of 2.5, 2.0 and 1.0 in a time to threshold (days) of 52, 42 and 42 respectively. These molecules also behaved in a somewhat intermediate fashion, exhibiting a reduced tendency to delay evaporation, and should be used sparingly, although in higher amounts than the group of molecules reported in the preceding paragraph, e.g. up to about 5 to 7%.

EXAMPLE 2

Consumer Testing:

Two fragrances were compared by a panel of 50 panelists, who assessed their hedonic pleasantness. The characteristics of these two perfumes are listed in Table I.

TABLE I

Characteristics of the perfumes assessed for hedonic pleasantness

| Ingredient groups | Perfume A | Perfume B |
| --- | --- | --- |
| Flexible musks of GROUP 1 (flexibility index > 45) | 0.2 | 1.2 |
| Flexible musks of GROUP 2 (19 < flexibility index <= 45) | 0.14 | 0.3 |
| Keto-esters | 2 | 1.7 |
| Terpene alcohols | 2.2 | 2 |
| Aromatic aldehydes | 1.6 | 1.4 |
| Alkyl aldehydes | 0.6 | 0.5 |
| Lactones | 0.7 | 0.6 |
| Polycyclic ketones | 0.4 | 0.4 |
| Heterocyclic compounds | 0.6 | 0.6 |
| Esters | 0.22 | 0.18 |
| Cyclic alcohols | 0.12 | 0.11 |
| Other minor perfumery ingredients | 1.02 | 0.91 |
| Solvent | 90.2 | 90.1 |
| Total | 100 | 100 |

The two perfumes had similar compositions, except Perfume B comprised an excess of flexible musk ingredients, according to the present invention.

The tests subjects were asked to choose a favourite fragrance. 28% of subjects chose the Perfumer A, which was a commercial fragrance, whereas 68% chose the fragrance B, which conforms to the present invention in containing higher levels of musk molecules.

The subjects were asked to rate the two fragrances for the following characteristics: Caring; Inviting; Soft/Gentle; Comforting; Fresh; Warm; Harsh/Irritating; Rough/Biting.

For the Perfume A the responses (%) were respectively: 32, 32, 32, 36, 32, 36, 28 and 28.

For the Perfume B, the responses (%) were respectively: 60, 52, 52, 52, 48, 52, 12 and 12.

The results clearly demonstrate that the fragrance containing musk was found significantly better in the positive characteristics, and was also deemed significantly less harsh/irritating and rough/biting.

Test Methodology

Blind sniff tests—Each fragrance was assigned a unique numeric code

The samples were enclosed within air care booths of 765 cubic feet in volume.

The test was a Sequential Monadic Paired Comparison Randomized Block Design—Fragrances evaluated sequentially in a pre-established randomized order The test subjects were females who were current liquid electrical air freshener devices users (Sample: n=50)

Two fragrances evaluated per test.

Protocol:
1. Evacuate two air care booths completely for 1 hour 2. Plug liquid electrical device into socket in booth and set to level '4' and let run for 1 hour to fully fill the air care evaluation booth to desired fragrance level.
3. Based upon randomized block design, instruct respondent to enter a booth.
4. Allow respondent 1-2 minutes to acclimatize to fragrance.
5. Hand respondent survey to complete within air care booth.
6. Once completed, instruct respondent to exit booth.
7. Allow respondent 4-5 minutes outside of evaluation booths to re-balance
8. Now instruct the respondent to enter the remaining booth, and follow protocol from step 4-7 above.
9. Once the respondent has completed both evaluations. Distribute the paired comparison test survey.
10. As respondent will now be making direct comparative judgments between the two fragrances, instruct the respondent that they may freely enter and leave each booth to familiarize themselves again to each fragrance. Allow respondent 4-5 minutes to compete this phase.
11. The evaluation is now complete.
12. After 1 hour of evaluations, evacuate booths per step 1 and repeat priming process.

Data were aggregated and analyzed to determine if statistically significant differences existed between the two fragrances tested.

There is therefore provided in a first embodiment, a method of creating a long-lasting and impactful fragrance formulation for air freshener applications that is capable of delivering olfactive impressions of softness, warmth, solidity and depth, comprising:

providing in a liquid composition, at least one fragrance ingredient selected from the group consisting of:
0.1% to 10% by weight of the total liquid composition of a fragrance ingredient, which is an Ingredient Group 1 ingredient; and/or
0.1% to 7% by weight of the total liquid composition of a fragrance ingredient, which is an Ingredient Group 2 ingredient; and/or
0 to 1% by weight of the total liquid composition of a fragrance ingredient, which is an Ingredient Group 3 ingredient;
wherein
the Ingredient Group 1 ingredient is a fragrance ingredient having a standard equilibrium headspace concentration (HS$_i$) of greater than 12 to 50 micrograms/litre, and a Flexibility Index (FI$_i$) of 45 or more;

the Ingredient Group 2 ingredient is a fragrance ingredient having a standard equilibrium headspace concentration between 5 and 12 micrograms/litre, and a Flexibility Index of 20 or greater; and the Ingredient Group 3 ingredient is a fragrance ingredient having a standard equilibrium headspace concentration of less than 5 micrograms/litre, and a Flexibility Index of 7 or greater.

According to the first embodiment, the Ingredient Group 2 ingredient may have a Flexibility Index between 20 and 44.

According to the first and subsequent embodiment, the Ingredient Group 3 ingredient may have a Flexibility Index between 7 and 19.

The first and subsequent embodiments may include determining the conformational mobility of the fragrance ingredients by calculating the Flexibility Index (FI$_i$) of the ingredients, wherein the structure of each ingredient is minimized by applying the default setting of LowModeMD search of the Energy minimisation menu in Molecular Operating Environment (MOE) by using the MMFF94 force field, the conformations of each molecule are generated by the default setting of LowModeMD search in MOE, and the water accessibility surface area values (ASA) of each conformation is computed in MOE by using a radius of 1.4 Å for the water molecule.

According to the first and subsequent embodiments, the at least one fragrance ingredient may be a musk.

According to the first and subsequent embodiments, the at least one fragrance ingredient may be selected from the group consisting of Cashmeran (1,1,2,3,3-pentamethyl-2,3,6,7-tetrahydro-1H-inden-4(5H)-one), Galaxolide (4,6,6,7,8,8-hexamethyl-1,3,4,6,7,8-hexahydrocyclopenta [g]isochromene), Galaxolide S ((4S)-4,6,6,7,8,8-hexamethyl-1,3,4,6,7,8-hexahydrocyclopenta[g]-2-benzopyran), Moxalone (1a,3,3,4,6,6-hexamethyl-1a,2,3,4,5,6,7,7a-octahydronaphtho[2,3-b]oxirene), Cosmone ((Z)-3-methylcyclotetradec-5-enone), Thibetolide (oxacyclohexadecan-2-one), Velvione ((Z)-cyclohexadec-5-enone), Muscenone ((Z)-3-methylcyclopentadec-5-enone), Nirvanolide ((E)-13-methyloxacyclopentadec-10-en-2-one), Habanolide ((E)-oxacyclohexadec-12-en-2-one), Civettone ((Z)-cycloheptadec-9-enone), C14 musk (1,4-dioxacyclohexadecane-5,16-dione), Ethylene Brassylate (1,4-dioxacycloheptadecane-5,17-dione), Ambrettolide ((Z)-oxacycloheptadec-10-en-2-one), Serenolide (2-(1-(3,3-dimethylcyclohexyl)ethoxy)-2-methylpropyl cyclopropanecarboxylate), Sylkolide ((E)-2-((3,5-dimethylhex-3-en-2-yl)oxy)-2-methylpropyl cyclopropanecarboxylate), Silvanone (blend of cyclopentadecanone and 1-oxacycloheptadecan-2-one), Musk CPD (cyclopentadecanone), Hexadecanolide (1-oxacycloheptadecan-2-one), (R,E)-2-methyl-2-((3-methylhex-3-en-2-yl)oxy)propyl cyclopropanecarboxylate, (R,E)-2-((3-ethyl-5-methylhex-3-en-2-yl)oxy)-2-methylpropyl cyclopropanecarboxylate, (R,E)-2-((3-ethyl-5-methylhex-3-en-2-yl)oxy)-2-methylpropyl propionate, (R,E)-2-((3-ethyl-5-methylhex-3-en-2-yl)oxy)-2-methylpropylcyclobutane carboxylate, (R,E)-2-((3,6-dimethylhept-3-en-2-yl)oxy)-2-methylpropylcyclopropane carboxylate, (E)-2-((3,5-dimethylhept-3-en-2-yl)oxy)-2-methyl propyl cyclopropane carboxylate, 2-((4-(cyclohex-3-en-1-yl)-3-methylbut-3-en-2-yl)oxy)-2-methyl propyl isobutyrate, and mixtures thereof.

According to the first and subsequent embodiments, the at least one fragrance ingredient may be selected from 0.1 to 10% by weight of Sylkolide ((E)-2-((3,5-dimethylhex-3-en-2-yl)oxy)-2-methylpropyl cyclopropanecarboxylate), from 0.1 to 7% of Cosmone ((Z)-3-methylcyclotetradec-5-enone), and/or from 0.1 to 7% of Serenolide (2-(1-(3,3-dimethylcyclohexyl)ethoxy)-2-methylpropyl cyclopropanecarboxylate).

According to the first and subsequent embodiments, the at least one fragrance ingredient may be selected from 0.1 to 10% by weight of Sylkolide ((E)-2-((3,5-dimethylhex-3-en-2-yl)oxy)-2-methylpropyl cyclopropanecarboxylate), from 3 to 5% of Cosmone ((Z)-3-methylcyclotetradec-5-enone), and/or from 5 to 7% of Serenolide (2-(1-(3,3-dimethylcyclohexyl)ethoxy)-2-methylpropyl cyclopropanecarboxylate).

According to the first and subsequent embodiments, Galaxolide S ((4S)-4,6,6,7,8,8-hexamethyl-1,3,4,6,7,8-hexahydrocyclopenta[g]-2-benzopyran), Musk CPD (cyclopentadecanone), Ethylene Brassylate (1,4-dioxacycloheptadecane-5,17-dione), Ambrettolide ((Z)-oxacycloheptadec-10-en-2-one), and Velvione ((Z)-cyclohexadec-5-enone) may not be used at all.

There is also provided in a second embodiment, a liquid electrical air care device comprising a reservoir for dispensing a liquid composition from the reservoir containing the liquid composition, wherein the liquid composition comprises:

0.1% to 10% by weight of the total liquid composition of a fragrance ingredient having a standard equilibrium headspace concentration (HS$_i$) of greater than 12 to 50 micrograms/litre, and a Flexibility Index (FI$_i$) of 45 or more; and/or 0.1% to 7% by weight of the total liquid composition of a fragrance ingredient, having a standard equilibrium headspace concentration between 5 and 12 micrograms/litre, and a Flexibility Index of between 20 and 44; and/or 0 to 1% by weight of the total liquid composition of a fragrance ingredient, having a standard equilibrium headspace concentration of less than 5 micrograms/litre, and a Flexibility Index of between 7 and 19.

According to the second embodiment, the at least one fragrance ingredient may be a musk.

According to the second and subsequent embodiment, the at least one fragrance ingredient may be selected from the group consisting of Cashmeran (1,1,2,3,3-pentamethyl-2,3,6,7-tetrahydro-1H-inden-4(5H)-one), Galaxolide (4,6,6,7,8,8-hexamethyl-1,3,4,6,7,8-hexahydrocyclopenta [g]isochromene), Galaxolide S ((4S)-4,6,6,7,8,8-hexamethyl-1,3,4,6,7,8-hexahydrocyclopenta[g]-2-benzopyran), Moxalone (1a,3,3,4,6,6-hexamethyl-1a,2,3,4,5,6,7,7a-octahydronaphtho[2,3-b]oxirene), Cosmone ((Z)-3-methylcyclotetradec-5-enone), Thibetolide (oxacyclohexadecan-2-one), Velvione ((Z)-cyclohexadec-5-enone), Muscenone ((Z)-3-methylcyclopentadec-5-enone), Nirvanolide ((E)-13-methyloxacyclopentadec-10-en-2-one), Habanolide ((E)-oxacyclohexadec-12-en-2-one), Civettone ((Z)-cycloheptadec-9-enone), C14 musk (1,4-dioxacyclohexadecane-5,16-dione), Ethylene Brassylate (1,4-dioxacycloheptadecane-5,17-dione), Ambrettolide ((Z)-oxacycloheptadec-10-en-2-one), Serenolide (2-(1-(3,3-dimethylcyclohexyl)ethoxy)-2-methylpropyl cyclopropanecarboxylate), Sylkolide ((E)-2-((3,5-dimethylhex-3-en-2-yl)oxy)-2-methylpropyl cyclopropanecarboxylate), Silvanone (blend of cyclopentadecanone and 1-oxacycloheptadecan-2-one), Musk CPD (cyclopentadecanone), Hexadecanolide (1-oxacycloheptadecan-2-one), (R,E)-2-methyl-2-((3-methylhex-3-en-2-yl)oxy)propyl cyclopropanecarboxylate, (R,E)-2-((3-ethyl-5-methylhex-3-en-2-yl)oxy)-2-methylpropyl cyclopropanecarboxylate, (R,E)-2-((3- ethyl-5-methylhex-3-en-2-yl)oxy)-2-methylpropyl propionate, (R,E)-2-((3-ethyl-5-methylhex-3-en-2-yl)oxy)-2-methylpropylcyclobutane carboxylate, (R,E)-2-((3,6-dimethylhept-3-en-2-yl)oxy)-2-methylpropylcyclopropane carboxylate, (E)-2-((3,5-dimethylhept-3-en-2-yl)oxy)-2-methylpropylcyclopropane carboxylate, 2-((4-(cyclohex-3-en-1-yl)-3-methylbut-3-en-2-yl)oxy)-2-methylpropyl isobutyrate, and mixtures thereof.

According to the second and subsequent embodiments, the at least one fragrance ingredient may be selected from 0.1 to 10% by weight of Sylkolide ((E)-2-((3,5-dimethylhex-3-en-2-yl)oxy)-2-methylpropyl cyclopropanecarboxylate), from 0.1 to 7% of Cosmone ((Z)-3-methylcyclotetradec-5-enone), and/or from 0.1 to 7% of Serenolide (2-(1-(3,3-dimethylcyclohexyl)ethoxy)-2-methylpropyl cyclopropanecarboxylate).

According to the second and subsequent embodiments, the liquid composition may comprise from 0.1 to 10% by weight of Sylkolide ((E)-2-((3,5-dimethylhex-3-en-2-yl)oxy)-2-methylpropyl cyclopropanecarboxylate), and/or from 3 to 5% of Cosmone ((Z)-3-methylcyclotetradec-5-enone), and/or from 5 to 7% of Serenolide (2-(1-(3,3-dimethylcyclohexyl)ethoxy)-2-methylpropyl cyclopropanecarboxylate).

There is also provided in a third embodiment, a method comprising utilizing in a liquid electrical air care device for dispensing a liquid composition, the liquid composition comprising:
- 0.1% to 10% by weight of the total liquid composition of a fragrance ingredient having a standard equilibrium headspace concentration ($HS_i$) of greater than 12 to 50 micrograms/litre, and a Flexibility Index ($FI_i$) of 45 or more; and/or
- 0.1% to 7% by weight of the total liquid composition of a fragrance ingredient, having a standard equilibrium headspace concentration between 5 and 12 micrograms/litre, and a Flexibility Index of between 20 and 44; and/or
- 0 to 1% by weight of the total liquid composition of a fragrance ingredient, having a standard equilibrium headspace concentration of less than 5 micrograms/litre, and a Flexibility Index of between 7 and 19.

According to the third embodiment, the fragrance ingredient may be a musk.

According to the third and subsequent embodiment, the fragrance ingredient may be selected from the group consisting of Cashmeran (1,1,2,3,3-pentamethyl-2,3,6,7-tetrahydro-1H-inden-4(5H)-one), Galaxolide (4,6,6,7,8,8-hexamethyl-1,3,4,6,7,8-hexahydrocyclopenta [g]isochromene), Galaxolide S ((4S)-4,6,6,7,8,8-hexamethyl-1,3,4,6,7,8-hexahydrocyclopenta[g]-2-benzopyran), Moxalone (1a,3,3,4,6,6-hexamethyl-1a,2,3,4,5,6,7,7a-octahydronaphtho[2,3-b]oxirene), Cosmone ((Z)-3-methylcyclotetradec-5-enone), Thibetolide (oxacyclohexadecan-2-one), Velvione ((Z)-cyclohexadec-5-enone), Muscenone ((Z)-3-methylcyclopentadec-5-enone), Nirvanolide ((E)-13-methyloxacyclopentadec-10-en-2-one), Habanolide ((E)-oxacyclohexadec-12-en-2-one), Civettone ((Z)-cycloheptadec-9-enone), C14 musk (1,4-dioxacyclohexadecane-5,16-dione), Ethylene Brassylate (1,4-dioxacycloheptadecane-5,17-dione), Ambrettolide ((Z)-oxacycloheptadec-10-en-2-one), Serenolide (2-(1-(3,3-dimethylcyclohexyl)ethoxy)-2-methylpropyl cyclopropanecarboxylate), Sylkolide ((E)-2-((3,5-dimethylhex-3-en-2-yl)oxy)-2-methylpropyl cyclopropanecarboxylate), Silvanone (blend of cyclopentadecanone and 1-oxacycloheptadecan-2-one), Musk CPD (cyclopentadecanone), Hexadecanolide (1-oxacycloheptadecan-2-one), (R,E)-2-methyl-2-((3-methylhex-3-en-2-yl)oxy)propyl cyclopropanecarboxylate, (R,E)-2-((3-ethyl-5-methylhex-3-en-2-yl)oxy)-2-methylpropyl cyclopropanecarboxylate, (R,E)-2-((3-ethyl-5-methylhex-3-en-2-yl)oxy)-2-methylpropyl propionate, (R,E)-2-((3-ethyl-5-methylhex-3-en-2-yl)oxy)-2-methylpropylcyclobutane carboxylate, (R,E)-2-((3,6-dimethylhept-3-en-2-yl)oxy)-2-methylpropylcyclopropane carboxylate, (E)-2-((3,5-dimethylhept-3-en-2-yl)oxy)-2-methylpropyl cyclopropane carboxylate, 2-((4-(cyclohex-3-en-1-yl)-3-methylbut-3-en-2-yl)oxy)-2-methylpropyl isobutyrate, and mixtures thereof.

According to the third and subsequent embodiments, the fragrance ingredient may be selected from 0.1 to 10% by weight of Sylkolide ((E)-2-((3,5-dimethylhex-3-en-2-yl)oxy)-2-methylpropyl cyclopropanecarboxylate), from 0.1 to 7% of Cosmone ((Z)-3-methylcyclotetradec-5-enone), and/or from 0.1 to 7% of Serenolide (2-(1-(3,3-dimethylcyclohexyl)ethoxy)-2-methylpropyl cyclopropanecarboxylate).

According to the third and subsequent embodiments, the fragrance ingredient may be selected from 0.1 to 10% by weight of Sylkolide ((E)-2-((3,5-dimethylhex-3-en-2-yl)oxy)-2-methylpropyl cyclopropanecarboxylate), from 3 to 5% of Cosmone ((Z)-3-methylcyclotetradec-5-enone), and/or from 5 to 7% of Serenolide (2-(1-(3,3-dimethylcyclohexyl)ethoxy)-2-methylpropyl cyclopropanecarboxylate).

The Flexibility Index in the above embodiments may be a known Flexibility Index.

It should be understood that the embodiments described above are not only in the alternative, but can be combined.

The invention claimed is:

1. A method of creating a long-lasting and impactful fragrance formulation comprising a liquid composition for air freshener applications that is capable of delivering olfactive impressions of softness, warmth, solidity and depth, comprising:
   determining the conformational mobility of the fragrance ingredients by calculating the Flexibility Index ($FI_i$) of the ingredients, wherein the structure of each ingredient is minimized by applying the default setting of LowModeMD search of the Energy minimisation menu in Molecular Operating Environment (MOE) by using the MMFF94 force field, the conformations of each molecule are generated by the default setting of LowModeMD search in MOE, and the water accessibility surface area values (ASA) of each conformation is computed in MOE by using a radius of 1.4 Å for the water molecule, the Flexibility Index is the difference between the maximum and minimum ASA values; and
   selecting at least one fragrance ingredient selected from the group consisting of:
   0.1% to 10% by weight of the total liquid composition of a fragrance ingredient, which is an Ingredient Group 1 ingredient,
   0.1% to 7% by weight of the total liquid composition of a fragrance ingredient, which is an Ingredient Group 2 ingredient,
   greater than 0 to 1% by weight of the total liquid composition of a fragrance ingredient, which is an Ingredient Group 3 ingredient, and
   mixtures thereof,
   wherein
   the Ingredient Group 1 ingredient is a fragrance ingredient having a standard equilibrium headspace concentration ($HS_i$) of greater than 12 to 50 micrograms/litre, and a Flexibility Index ($FI_i$) of 45 or more;
   the Ingredient Group 2 ingredient is a fragrance ingredient having a standard equilibrium headspace concentration between 5 and 12 micrograms/litre, and a Flexibility Index of 20 or greater; and the Ingredient Group 3 ingredient is a fragrance ingredient having a standard equilibrium headspace concentration of less than 5 micrograms/litre, and a Flexibility Index of 7 or greater; and adding together said selected fragrance ingredients to create said fragrance formulation.

2. The method according to claim 1, wherein the Ingredient Group 2 ingredient has a Flexibility Index between 20 and 44.

3. The method according to claim 1, wherein the Ingredient Group 3 ingredient has a Flexibility Index between 7 and 19.

4. The method according to claim 1, wherein the at least one fragrance ingredient is a musk.

5. The method according to claim 1, wherein the at least one fragrance ingredient is selected from the group consisting of Cashmeran (1,1,2,3,3-pentamethyl-2,3,6,7-tetrahydro-1H-inden-4(5H)-one, an Ingredient Group 1 ingredient), Galaxolide (4,6,6,7,8,8-hexamethyl-1,3,4,6,7,8-hexahydrocyclopenta [g]isochromene, an Ingredient Group 3 ingredient), Galaxolide S ((4S)-4,6,6,7,8,8-hexamethyl-1,3,4,6,7,8-hexahydrocyclopenta[g]-2-benzopyran, an Ingredient Group 3 ingredient), Moxalone (1a,3,3,4,6,6-hexamethyl-1a,2,3,4,5,6,7,7a-octahydronaphtho[2,3-b]oxirene, an Ingredient Group 1 ingredient), Cosmone ((Z)-3-methylcyclotetradec-5-enone, an Ingredient Group 2 ingredient), Thibetolide (oxacyclohexadecan-2-one, an Ingredient Group 2 ingredient), Velvione ((Z)-cyclohexadec-5-enone, an Ingredient Group 1 ingredient), Muscenone ((Z)-3-methylcyclopentadec-5-enone, an Ingredient Group 2 ingredient), Nirvanolide ((E)-13-methyloxacyclopentadec-10-en-2-one, an Ingredient Group 2 ingredient), Habanolide ((E)-oxacyclohexadec-12-en-2-one, an Ingredient Group 3 ingredient), Civettone ((Z)-cycloheptadec-9-enone, an Ingredient Group 3 ingredient), C14 musk (1,4-dioxacyclohexadecane-5,16-dione, an Ingredient Group 3 ingredient), Ethylene Brassylate (1,4-dioxacycloheptadecane-5,17-dione, an Ingredient Group 3 ingredient), Ambrettolide ((Z)-oxacycloheptadec-10-en-2-one, an Ingredient Group 3 ingredient), Serenolide (2-(1-(3,3-dimethylcyclohexyl)ethoxy)-2-methylpropyl cyclopropanecarboxylate, an Ingredient Group 3 ingredient), Sylkolide ((E)-2-((3,5-dimethylhex-3-en-2-yl)oxy)-2-methylpropyl cyclopropanecarboxylate, an Ingredient Group 1 ingredient), Silvanone (blend of cyclopentadecanone, an Ingredient Group 3 ingredient and 1-oxacycloheptadecan-2-one, an Ingredient Group 3 ingredient), Musk CPD (cyclopentadecanone, an Ingredient Group 3 ingredient), Hexadecanolide (1-oxacycloheptadecan-2-one, an Ingredient Group 3 ingredient), (R,E)-2-methyl-2-((3-methylhex-3-en-2-yl)oxy)propyl cyclopropane carboxylate (an Ingredient Group 1 ingredient), (R,E)-2-((3-ethyl-5-methylhex-3-en-2-yl)oxy)-2-methylpropylcyclopropane carboxylate (an Ingredient Group 1 ingredient), (R,E)-2-((3-ethyl-5-methylhex-3-en-2-yl)oxy)-2-methylpropyl propionate (an Ingredient Group 1 ingredient), (R,E)-2-((3-ethyl-5-methylhex-3-en-2-yl)oxy)-2-methylpropylcyclobutanecarboxylate (an Ingredient Group 2 ingredient), (R,E)-2-((3,6-dimethylhept-3-en-2-yl)oxy)-2-methylpropylcyclopropanecarboxylate (an Ingredient Group 1 ingredient), (E)-2-((3,5-dimethylhept-3-en-2-yl)oxy)-2-methylpropyl cyclopropane carboxylate (an Ingredient Group 1 ingredient), 2-((4-(cyclohex-3-en-1-yl)-3-methylbut-3-en-2-yl)oxy)-2-methylpropyl isobutyrate (an Ingredient Group 3 ingredient), and mixtures thereof.

6. The method according to claim 1, wherein the at least one fragrance ingredient is selected from the group consisting of 0.1 to 10% by weight of Sylkolide ((E)-2-((3,5-dimethylhex-3-en-2-yl)oxy)-2-methylpropyl cyclopropanecarboxylate, (an Ingredient Group 1 ingredient), from 0.1 to 7% of Cosmone ((Z)-3-methylcyclotetradec-5-enone (an Ingredient Group 2 ingredient), from 0.1 to 7% of Serenolide (2-(1-(3,3-dimethylcyclohexyl)ethoxy)-2-methylpropyl cyclopropanecarboxylate (an Ingredient Group 3 ingredient), and mixtures thereof.

7. The method according to claim 1, wherein the at least one fragrance ingredient is selected from the group consisting of 0.1 to 10% by weight of Sylkolide ((E)-2-((3,5-dimethylhex-3-en-2-yl)oxy)-2-methylpropyl cyclopropanecarboxylate (an Ingredient Group 1 ingredient), from 3 to 5% of Cosmone ((Z)-3-methylcyclotetradec-5-enone (an Ingredient Group 2 ingredient), from 5 to 7% of Serenolide (2-(1-(3,3-dimethylcyclohexyl)ethoxy)-2-methylpropyl cyclopropanecarboxylate (an Ingredient Group 3 ingredient), and mixtures thereof.

8. The method according to claim 1, wherein Galaxolide S ((4S)-4,6,6,7,8,8-hexamethyl-1,3,4,6,7,8-hexahydrocyclopenta[g]-2-benzopyran (an Ingredient Group 3 ingredient), Musk CPD (cyclopentadecanone (an Ingredient Group 3 ingredient), Ethylene Brassylate (1,4-dioxacycloheptadecane-5,17-dione (an Ingredient Group 3 ingredient), Ambrettolide ((Z)-oxacycloheptadec-10-en-2-one (an Ingredient Group 3 ingredient), and Velvione ((Z)-cyclohexadec-5-enone (an Ingredient Group 3 ingredient) are not used at all.

* * * * *